United States Patent [19]

Cowdery

[11] 4,399,819

[45] Aug. 23, 1983

[54] HEART PACER MECHANICAL CONSTRUCTION

[75] Inventor: David Cowdery, East Ballina, Australia

[73] Assignee: Telectronics Pty. Ltd., Lane Cove, Australia

[21] Appl. No.: 332,922

[22] Filed: Dec. 21, 1981

[51] Int. Cl.³ .............................................. A61N 1/36
[52] U.S. Cl. ........................... 128/419 P; 128/419 PS
[58] Field of Search ....... 128/419 P, 419 PG, 419 PS, 128/419 PT, 419 B, 419 C, 419 D

[56] References Cited

U.S. PATENT DOCUMENTS

| 3,822,707 | 7/1974 | Adducci et al. | 128/419 PS X |
| 3,926,198 | 12/1975 | Kolenik | 128/419 PS X |
| 4,041,956 | 8/1977 | Purdy et al. | 128/419 PS X |
| 4,245,642 | 1/1981 | Skubitz et al. | 128/419 P |
| 4,254,775 | 3/1981 | Langer | 128/419 PS X |
| 4,262,673 | 4/1981 | Kinney et al. | 128/419 P |

FOREIGN PATENT DOCUMENTS

142844  7/1980  Fed. Rep. of Germany ... 128/419 P

Primary Examiner—Kyle L. Howell
Assistant Examiner—Angela D. Sykes
Attorney, Agent, or Firm—Gottlieb, Rackman & Reisman

[57] ABSTRACT

There is disclosed a three-board electronic assembly construction for a heart pacer which solves the numerous problems presented by prior art two-board assemblies without increasing the pacer size. The size of the unit is also held to a minimum by providing a simple flat sheet of resilient material for constraining all of the sub-assemblies within the pacer case, and by judiciously placing two RF filter capacitors in the region of the terminal assembly the capacitors do not add to the bulk of the overall unit.

27 Claims, 8 Drawing Figures

HEART PACER MECHANICAL CONSTRUCTION

DESCRIPTION

This invention relates to heart pacers, and more particularly to the mechanical constructions thereof.

An important objective in the design of any implantable heart pacer is size reduction. Throughout the years, implantable heart pacers have become smaller and smaller. In recent years, however, new functions have been added to heart pacers and this has necessarily resulted in an increase in the number of required integrated circuits and discrete components. Especially in the case of a dual-chamber pacer, which in effect consists of one control and two pacing mechanisms in one housing, there is a great need to pack the components more tightly if minimal size objectives are to be achieved.

The four basic sub-systems of a heart pacer are the battery or power cell, the electronic circuit assembly which contains the control and pulsing circuits, the case which is usually hermetically sealed in order to protect the pacer mechanism from exposure to body fluids, and the terminal assembly which includes both a case cover and one or more "lead-throughs" which allow the conductors connected to the stimulating electrodes to be coupled to the interior of the generator. It is the electronic assembly whose volume poses the biggest problem as more and more functions are added to a heart pacer; the circuit boards on which the integrated circuits and discrete components are mounted must become larger as more integrated circuits and components are added.

A typical prior art heart pacer electronic assembly consists of two printed circuit boards. A metallization pattern is etched on each board, often on both sides, as in the case of any printed circuit board. But instead of mounting the integrated circuits and components on individual boards, for the most part they are often mounted between the boards. For example, a resistor might extend in a direction perpendicular to both boards with both of its leads being soldered to different boards. The integrated circuits which are utilized often straddle two edges of the boards. As in the case of the discrete components, the integrated circuits are placed between the boards. The pins on either side of an integrated circuit (or, more accurately, the integrated circuit package) are bent so that they can contact respective outer faces of the two boards, at which contact points they are soldered. The several integrated circuits are mounted along the peripheries of the printed circuit boards. While some discrete components are mounted on individual boards, the integrated circuit packages take up so much room that it is often impractical to mount any of them on individual boards.

There are several problems with this prior art type of construction. First, the soldering process is very time-consuming because discrete components must be centered between the boards and held in place as they are soldered. There are often many cross-wires which extend between the two boards and are soldered to them, the wires serving not only as electrical connections but also to provide mechanical support. While the soldering of a cross-wire poses no problem in this regard because there is nothing to center, the same is not true of the many discrete components which extend between the boards.

The two-board construction with discrete components extending from board to board also makes the inspection and cleaning processes much more difficult. The individual boards cannot be inspected and/or cleaned because many of the components are soldered to both boards and there is no way to separate the boards to inspect or clean them without taking apart the circuit. Were the components to be mounted on individual boards, it would be much simpler to inspect the boards following assembly, and to clean them.

In the event testing of the electronic assembly reveals that there is a malfunction, it is often very difficult to replace a component which is determined to be defective. This is because the components are imbedded between the two boards and to replace a defective component it is often necessary to desolder all of them so that the boards can be separated. In practice, what often happens is that the entire assembly is simply discarded, at considerable cost.

Another problem of concern with two-board designs relates to the integrated circuit packages which straddle the boards. During handling of the electronic assembly, as the overall pacer is constructed, the boards sometimes flex and thus considerable stresses develop in the chip pins where they enter the integrated circuit package. Another problem with the straddling of the boards by the integrated circuit packages is that the pins must be bent in order for them to be soldered to the boards. This not only requires special tooling and additional labor, it also sometimes gives rise to damaging of the integrated circuits.

It might be thought that the problems enumerated above could be solved with the use of more than two printed circuit boards, especially if additional "real estate" is required in order to accommodate the many integrated circuits and discrete components which are required, for example, in a dual-chamber pacer. However, most workers in the field have been of the belief that even a three-board design would not be practical. While the additional board area which would result from the use of a third board might allow the discrete components and the integrated circuit packages to be mounted on individual boards with perhaps no cross-components and just cross-wires, the use of three parallel boards would necessarily increase the thickness of the overall pacer. Insofar as pacer size is concerned, perhaps the most important dimension whose size is to be kept to a minimum is that of thickness.

It is a general object of my invention to provide a three-board electronic assembly for a heart pacer which allows the final thickness of the pacer to be comparable to those of present-day units. (In the illustrative embodiment of the invention, the final pacer thickness has a nominal dimension of only 12 mm, which is quite small by present-day standards.)

Another problem with present-day pacers relates to the fit of the several sub-assemblies within the case. A heart pacer must be sufficiently robust to be able to withstand the vibrations encountered during transport, storage and use; the unit must not fail due to excessive stress being applied to the internal components. The manner in which the several sub-assemblies are packed together is of critical importance to device reliability. In addition to the main sub-assemblies described above, a typical heart pacer includes other components such as insulators, washers and terminals, etc. Because the several internal components and sub-assemblies are made from different materials and by different processing techniques, it is almost impossible to attain exact component fit between the case and the case cover, and the internal components. In order to prevent the internal sub-assemblies from vibrating within the case, there must be some way to constrain them.

One common technique is to use a casting material such as a silicone elastomer or epoxy resin to encase the internal sub-assemblies and components. Typically, the casting material is poured into the case after assembly. The disadvantages of this approach are well known to those skilled in the art. For one thing, after casting it is almost impossible to make any changes in the electronic assembly. Also, the use of a casting material not only increases the weight of the overall unit, but high stress levels may develop due to shrinkage of the casting material. There is also a greater risk of contamination, by contaminants which may be contained in the casting material, which may lead to the formation of dendritic growths and therefore short circuits.

Another prior art approach for constraining the internal sub-assemblies is to form a thermoplastic molding for the several sub-assemblies. The molding also serves to insulate the internal components from the case. The disadvantage of such a system, however, is that the molding adds significantly to the volume and size of the overall unit because precision moldings require wall thicknesses which tend to be significant when compared to the dimensions of the sub-assemblies themselves.

It has also been proposed to use coil springs and leaf springs for constraint purposes, usually in conjunction with thermoplastic moldings. But coil springs usually have a significant compressed length and require support frames, so they are not practical. Leaf springs must possess a considerable thickness to generate a useful constraining force because they must bend around an axis perpendicular to their length, thus increasing the overall size of the unit, not to mention that it may not be possible to bend them completely flat which would also tend to increase the unit size.

It has also been proposed to use adhesives to interconnect the several sub-assemblies. But adhesives also prevent repair work, and there are reliability problems associated with adhesive bonding to the typical components which are found in heart pacers. Two prior art patents which illustrate typical present-day constraining techniques are U.S. Pat. Nos. 4,041,956 and 4,243,042.

In accordance with the principles of my invention, I provide a three-board electronic assembly which, while accommodating additional components, minimizes the problems inherent in two-board designs. Additional functions can thus be provided, and they can be provided in a unit whose size is comparable to those of the prior art. I also provide a simple mechanism for constraining all of the sub-assemblies within the case, in such a manner that there is no significant increase in unit size.

The use of three boards, the size of each of which is comparable to the size of each board in a typical prior art two-board assembly, provides so much additional board area that it is possible to mount almost all of the components on individual boards. This is true even of the integrated circuit packages which no longer have to straddle two boards. In order to keep the thickness of the finished unit to a minimum, the two outside boards should have their attached components facing inwardly; this way, a flat board surface, a surface with a metallization pattern and on which soldering takes place, can be placed flush against each side of the case (with appropriate insulation, as will be described below). With the components of the two outer boards thus facing inwardly, it is apparent that the components on the inner board must face the components on one of the outer boards. It is this facing of components which might be though to necessitate an increase in overall thickness. However, there is in fact no increase in overall thickness. The reason for this is that the components on the two boards whose components face each other are positioned on the respective boards such that the components on each board extend into spaces between components on the other board. The distance between the two boards whose components face each other is thus approximately equal to the highest of all of the components contained on the boards. In the illustrative embodiment of the invention, one of these two boards has mounted on it several capacitors, the heights of these capacitors being greater than that of all of the other components. (By "height" is meant the distance along which a component extends up from the board on which it is mounted.) It will become apparent below that the distance between these two boards is approximately the same as the height of these capacitors. Insofar as the other outer board is concerned, it is spaced from the non-component side of the middle board by a distance equal approximately to the height of the highest component on the outer board.

During the design process, the electronic circuit is partitioned into three sections, each section corresponding to one board; the goal is to partition the overall circuit such that all connections to any individual component or integrated circuit are made on the same board. There are no hard and fast rules to follow in this regard, and there are usually many ways in which any particular circuit can be partitioned so as to fulfill or nearly fulfill the design goal. Ideally, the only board-to-board connections consist of cross-wires which are required anyway for mechanical rigidity. The cross-wires serve to interconnect the three partitioned sub-circuits on the three different boards. However, there may be cases in which it is not possible to completely eliminate the need to connect a particular component to two different boards. In the illustrative embodiment of the invention, the partitioning was such that one component, the reed switch which is found in most present-day heart pacers and which serves to control external programming of the unit, required one of its leads to be connected to one board and the other of its leads to be connected to another. It might be thought that the way to connect such a component between two boards is to position one of the boards in the middle, with the other board necessarily being one of the two outer boards, and to place the component between the boards in an orientation which is parallel with them; one lead would be bent toward one board and the other would be bent in the other direction toward the other board. This cannot be done, however, because the external programmer requires that the reed switch be oriented with its axis perpendicular to the planes of the boards.

The two boards to which the component must be connected are made the outer boards and the component itself extends in a direction perpendicular to the planes of the boards, just as in a two-board design. A hole is provided in the middle board so that the component can extend through it. It is thus apparent that even when the partitioning is not "perfect", the overall thickness of the electronic assembly need not increase unduly as a result of the need to place a component between two adjacent boards for connection to them. All that is necessary is to provide a hole in the middle board. Holes may also be provided in the middle board through which cross-wires extend in those cases where the wires must be connected only to the two outer boards. There are, of course, cross-wires between each pair of adjacent boards not only in order to provide the necessary electrical connections, but also to rigidly secure the boards to each other.

An added advantage of this design approach is that the individual boards may be tested during an early stage of production, before they are interconnected. In the prior art two-board design, there is really no "circuit" which can be tested until after the components are soldered in place between the two boards. But when almost all of the components are contained on individual boards, complete testing of individual boards is possible at an early stage in the production cycle. This leads to considerable economies as defective boards are found before the manufacturing process has advanced to later stages.

The several sub-assemblies are constrained within the case without the need for any casting materials, thermoplastic moldings, coil or leaf springs, etc. I have discovered that all that is required is the use of a simple thin sheet of polymeric material or metal placed between the usual curved surfaces of the battery casing and the outside case. (As used below, the term "battery" sometimes refers to the battery together with its shell, the sheet being placed between the shell and the outside case, and the "battery" thus including its shell.) The sheet may be totally unformed as in the illustrative embodiment of the invention, or partially pre-curved. In any event, it is placed at the bottom of the case, with the battery shell bearing against it. In a typical heart pacer design, the bottom of the case is curved. The battery casing and shell have a similar shape so that they can be fitted in the case. Simply placing a thin sheet of material between the bottom of the battery casing and the inner surface of the bottom of the overall case, with the edges of the sheet necessarily bending upward as the battery casing is pushed down in the case, causes the sheet to apply an upward force against the bottom of the battery casing which is sufficient to constrain all of the elements within the case. The battery bears against the electronic assembly which is disposed above it, and the electronic assembly bears against the several elements which separate the top of the electronic assembly and the case cover. It is to be noted that an elastomeric material at the bottom of the case to serve the same purpose is not preferred because these materials contain contaminants and could affect reliability, and designing with them is difficult because of the uncertainty in their minimum compressed thickness. A thin sheet of polymeric material or metal is sufficient to provide the required compression forces, due to the bending across the width of the sheet which necessarily results as the battery or its shell is placed within the case and forced against the sheet.

There is one other object of the invention which can be best understood only upon considering the actual mechanical construction to be described in detail below. A typical dual-chamber heart pacer includes two filter capacitors, each for connecting one of the stimulating electrode terminals to ground (the case of the unit). A typical present-day heart pacer also includes a thin polyimide flexible insulating sheet for restraining the wires which extend up from the electronic assembly to the terminal assembly. In accordance with the principles of my invention I provide a metallization layer on this insulating retainer to which two "chip" capacitors are directly soldered. The arrangement is such that the capacitors are connected in the circuit as required near the terminals, yet they in no way add to the bulk of the overall unit.

Further objects, features and advantages of my invention will become apparent upon consideration of the following detailed description in conjunction with the drawing, in which.

Figure 1:
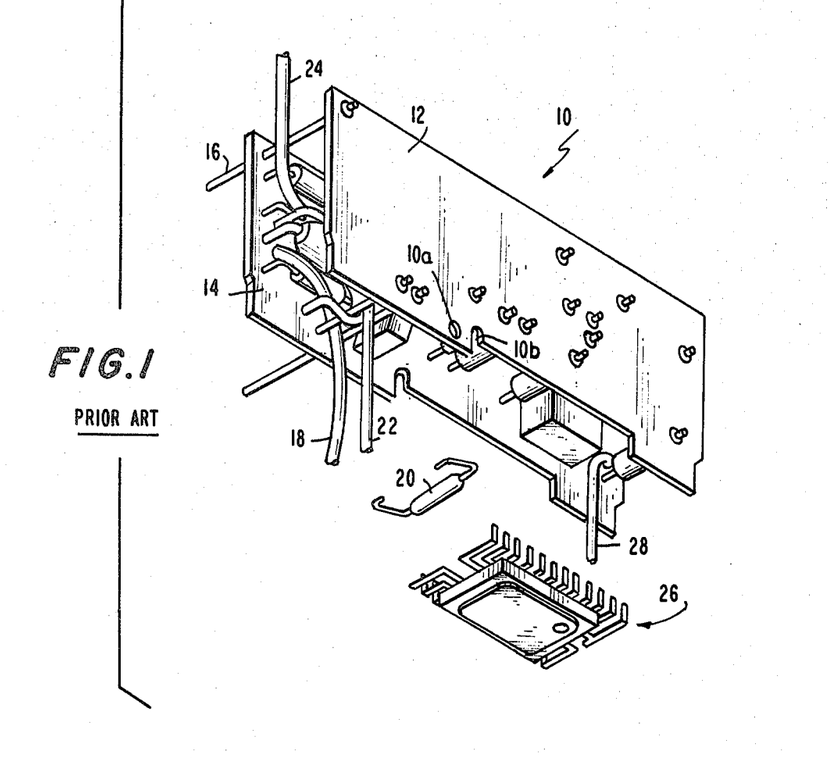
FIG. 1 depicts a typical prior art two-board heart pacer electronic assembly.

The two-board electronic assembly of FIG. 1 illustrates a typical prior art construction. The assembly 10 consists of two printed circuit boards 12, 14. There are metallization patterns on each side of each board, although they have been omitted from the drawing for the sake of clarity. Extended between the boards are a plurality of components, some of which are mounted on individual boards but others of which have their ends connected to different boards. Several wires are shown connected to the electronic assembly. Wire 24 extends up to an electrode terminal. (The two-board circuit of FIG. 1 is designed for use in a single-chamber pacer which has only one stimulating electrode terminal.) Wire 18 is connected to the negative terminal of the battery which is disposed underneath the electronic assembly, and wire 28 is connected to the positive terminal. Wire 22 is extended to an internal terminal which grounds the overall circuit to the case.

Integrated circuit package 26 is provided with bent pins along each of its sides. The package is placed in a straddle position between the two boards, with the pins on each side being soldered to the outer face of a respective board. Several such integrated circuits may be mounted on the two boards around their peripheries.

Wire 16 is a typical cross-wire which extends between the two boards and serves to establish not only an electrical connection but also to maintain the boards in position relative to each other. During production, several of the cross-wires may extend out of one or both of the boards to facilitate testing of the assembly. The wires are cut before final assembly.

One of the biggest problems with a construction of the type depicted in FIG. 1 pertains to the removal of components should that be necessary. There are several prior art techniques for simplifying component removal. One such technique is depicted in FIG. 1. Reed switch 20 is mounted not with its pins extending into the inner faces of the two boards, but rather with its pins directed into the outer faces of the two boards. As shown in FIG. 1, each lead is placed within a notch 10b, with the tip of the lead being bent and inserted into a hole 10a where it is soldered. This construction allows the component to be removed with a minimum of effort. However, for the most part it is not possible to remove components, especially those which are blocked by others, and repair of the electronic assembly often requires considerable dismantling and separation of the two boards.

Figure 2:
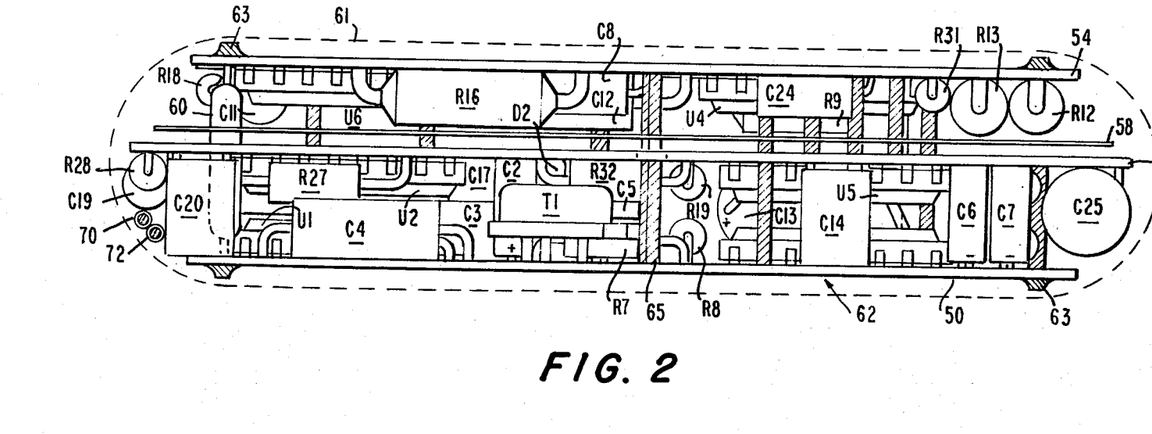
FIG. 2 is a sectional view of a three-board electronic assembly constructed in accordance with the principles of my invention.

FIG. 2 depicts a sectional view of a three-board electronic assembly 62 constructed in accordance with the principles of my invention. The three boards bear the numerals 50, 52 and 54. (The numeral 58 does not refer to a printed circuit board; element 58 is simply an insulator sheet with holes in it through which cross-wires and reed switch 60 pass. The sheet is used to physically separate the components on board 54 from the metallization pattern on the non-component side of board 52.) Cross-wires such as 65 are soldered to outer boards 50 and 54 while passing through board 52 without making any electrical contact. Others of the cross-wires are connected between boards 50 and 52, and boards 52 and 54. FIG. 2 is a top view of the electronic assembly, shown against the outlines of the internal case dimensions, the inside surface of the case being shown by the dashed lines 61. Only the four extreme solder joints 63 are shown in the drawing in order not to unduly complicate it. The drawing also shows two leads 70 and 72, which will be described in considerable detail below. These two leads exit the electronic assembly and extend upward for connection to the atrial and ventricular stimulating electrode terminals.

Several components are shown in FIG. 2 between adjacent printed circuit boards. The prefixes R, C, U, T and D refer respectively to resistors, capacitors, integrated circuit packages, transistors and diodes. The detailed circuitry is unimportant for an understanding of the present invention, as is the particular partitioning scheme. What is important to note is that almost all of the components are mounted on individual boards (the only exception being reed switch 60), and the spacing between boards is determined by the maximum height of any component on a board. The separation between boards 50 and 52 is determined by the heights of capacitors C6, C7, C14 and C20. These capacitors do not include terminals which are connected one to each board. Instead, each capacitor has two terminals on the same side, both of which are connected to the same board. All of the components on boards 50 and 52 are arranged such that they extend into spaces between the components on the other board. For example, it will be noted that resistor R27, whose two leads are connected to board 52, actually extends down past a level above which capacitor C4 on board 50 extends. Were these two components to face each other, obviously the distance between the two boards would have to be increased. But by positioning the components so that resistor R27 extends into a "clear" space on board 50, and by positioning capacitor C4 so that it extends into a "clear" space between components on board 52, the separation between the boards can be limited to the height of the component on the two boards which extends farthest away from its respective board.

Insofar as boards 52 and 54 are concerned, the spacing between them is determined by the largest components on board 54, which in this case are several components which have the same height, e.g., resistor R16.

With the particular partitioning scheme selected for the electronic assembly of FIG. 2, it turned out that reed switch 60 had to be connected to two different boards. While the reed switch could have been given an orientation such as that of resistor R16, with one lead being bent upward and another lead being bent downward so that the switch could be connected to two different boards, what is preferred is to place the component in an orientation which is perpendicular to the planes of the boards and connecting its two leads to the two outer boards, in this case boards 50 and 54. A hole is provided in board 52 through which the reed switch passes.

The intersecting thing to note is that were the circuit of the heart pacer of the illustrative embodiment of the invention to be assembled on two boards, along the lines of the prior art depicted in FIG. 1, the two boards would necessarily be spaced apart by more than the spacing between outer boards 50 and 54. This is because not only would reed switch 60 still have to be placed between them, but an even greater separation would be required to accommodate longer components such as resistor R16. Thus the three-board design actually permits a thinner construction than that which would be necessary were the prior art approach of FIG. 1 to be followed.

One of the most important aspects of the construction is that none of the integrated circuits has its pins connected to different boards, with the integrated circuit straddling the boards. Each package is contained only on a single board, thus minimizing the possibility of pin breakage during handling.

Figures 3, 4:
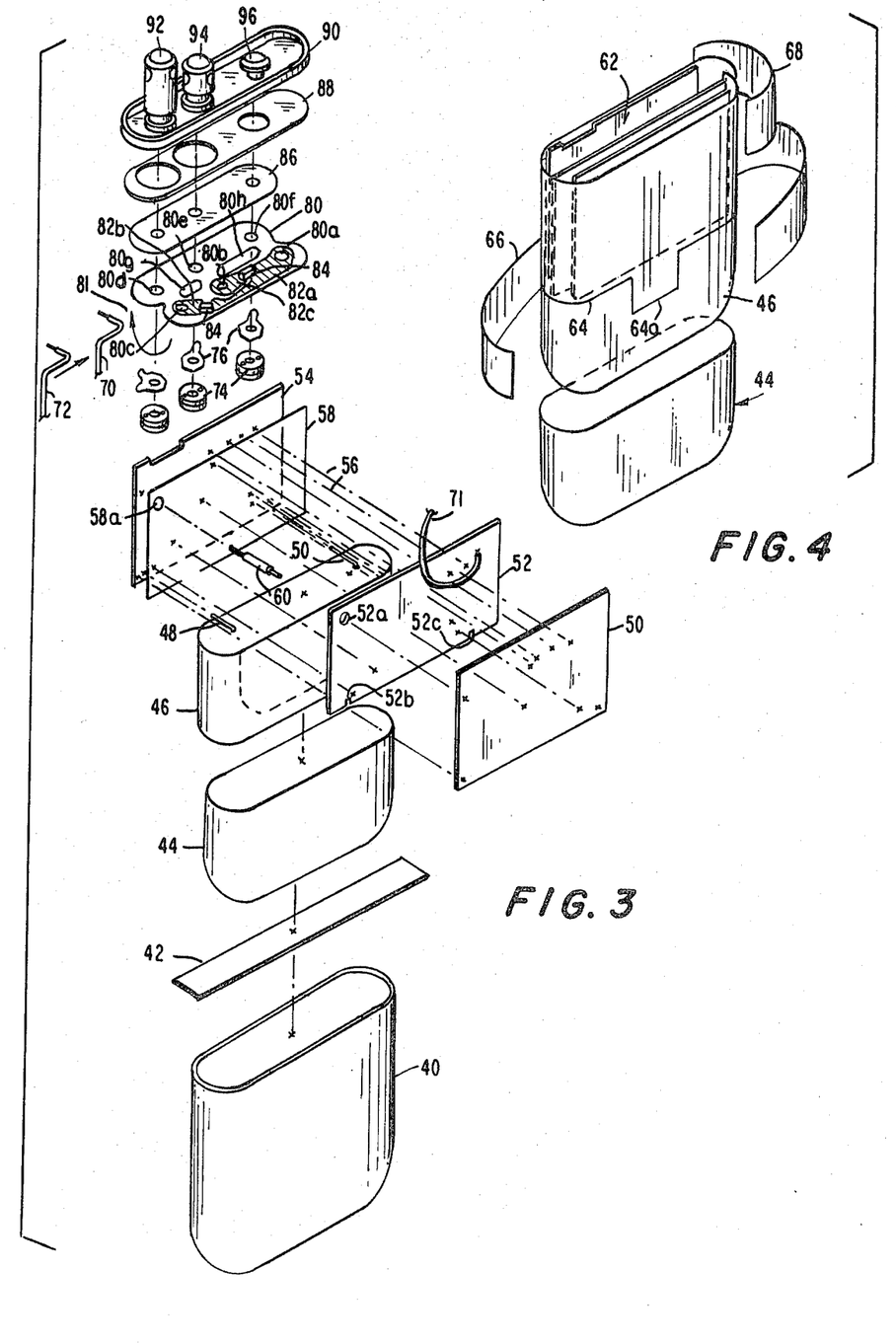
FIG. 3 is an exploded view showing the arrangement of all key components in the illustrative embodiment of the invention.
FIG. 4 depicts some of the key components assembled together together with additional insulating strips.
Figure 6:
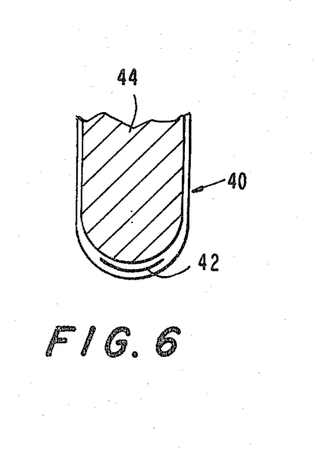
FIG. 6 is a sectional view through the case and battery casing of FIG. 3, and is designed to show the position of sheet 42 which constrains the various sub-assemblies.
Figure 7:
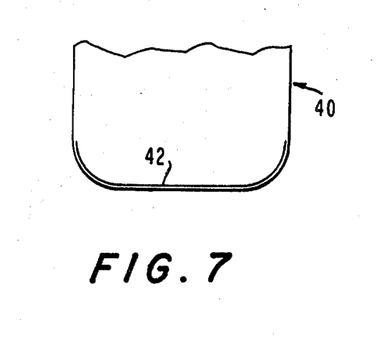
FIG. 7 is a front view of the case of FIG. 3, and further shows the shape of the compression sheet at the bottom thereof.

The exploded view of FIG. 3 depicts the major components of the pacer. Flat sheet 42 is made of material such as Dupont KAPTON, a polyimide film which is 0.08 mm thick. (Hard-drawn phosphor bronze of 0.025 mm thickness has also been found to be satisfactory.) The sheet is placed at the bottom of case 40, FIG. 6 showing the width of the sheet relative to the thickness of the case (the sheet typically has a width 50–60% of the pacer thickness of 10 mm), as well as the manner in which the sheet curves around one axis when battery shell 44 bears down against it; FIG. 7 depicts the manner in which the sheet may curve around a second axis, thus tending to centrally locate the sheet. The length of the sheet is equal to the length of the flat base of the case plus the sum of the lengths of the two rounded corners, each corner having a cross-sectional shape of a quarter-circle. As is evident from FIG. 6, when battery 46, or shell 44 if it is used, is focused down against the sheet, the sheet exerts an upward force against the battery because of the way in which it curves along an axis which is parallel with its length. Element 44 (which is sometimes omitted) is simply a TEFLON vacuum-formed shell which surrounds battery 46 so as to insulate it from the case 40 if such insulation is needed.

The three boards 50, 52 and 54 which comprise the electronic assembly are shown without any connected components for the sake of clarity. The lines which are shown extended between the boards represent cross-wires. The only component which is shown is reed switch 60. Its two leads are soldered to boards 50 and 54, a hole 52a being provided in board 52 and a hole 58a being provided in insulating sheet 58 to allow the reed switch to pass through these two elements. Only one lead 71 is shown extending up out of the electronic assembly, this lead coming from board 52 and serving as the ground lead; the connection of the lead to elements above it will be described below. Two other leads 70 and 72 are shown at the left of the drawing, and these two leads also come from the electronic assembly (not shown). These two leads serve to connect the electronic assembly to the atrial and ventricular stimulating electrode terminals, as will be described below.

Insofar as the electronic assembly is concerned, there is one other feature of considerable importance and that relates to battery pins 48 and 50. In prior art pacer mechanical constructions, wires and brackets are used to connect the two battery terminals to one or more circuit boards; alternatively metal clips have been provided, each clip being soldered to both one of the battery terminals and to the electronic assembly. In order to avoid the additional labor and in order to reduce the number of solder joints necessary to connect the battery to the circuit, the battery is provided with two pins which are bent just as they exit the battery casing. (Although not clear from the drawing, the top of the battery casing is provided with an insulating sheet, as is known in the art.) The two pins pass through holes in insulating sheet 58 and are soldered directly to board 54. Not only is there less labor required and fewer solder joints necessary, but it is also possible to reduce the overall height of the pacer by minimizing the separation between the top of the battery casing and the bottom of the electronic assembly.

One problem in this regard, however, is that board 52 could not ordinarily extend down as far as boards 50 and 54 because the bottom of board 52 would necessarily strike the bent battery pins. In order to avoid reducing the size of board 52, it is provided with two notches 52b and 52c which allow the battery pins to pass through them, thus not restricting the downward extension of the board. While in a two-board design it is possible to have the two boards separated by a distance greater than the thickness of the battery casing and thus actually extending down past the bottom of the battery casing, in a three-board design there would necessarily be interference with the middle board were it not for the provision of the notches. (Preferably, all three boards have their edges resting on top of the battery so as to prevent bending moments from developing on the battery pins.)

The numeral 90 represents the case cover. Atrial stimulating electrode terminal 92 is secured to the case cover with a brazed bushing, and a ceramic insulator is provided as is known in the art for insulating the terminal from the case cover. The terminal includes a pin (not shown) whose lower end is threaded and which passes through several holes in other elements for ultimate connection to one of the three nut terminals 74. Similar remarks apply to ventricular stimulating electrode terminal 94. The numeral 96 represents a reinforcing stud which makes electrical contact with the case cover and which also has a pin whose end is threaded for connection to one of nut terminals 74. This latter connection establishes a ground connection of wire 71 to the case. (The conventional Silastic top cap which is placed on top of the case cover 90 is not shown in the drawing.)

Heat shield 88, made of copper alloy, is the conventional shield which serves as a heat sink during the hermetic sealing of the case cover to the case in order to protect the internal parts from overheating during the welding process. The numeral 86 is simply a sheet of insulating mica, as is known in the art. Both the heat shield and the mica sheet are provided with holes through which the threaded pins described above pass.

Figure 5:
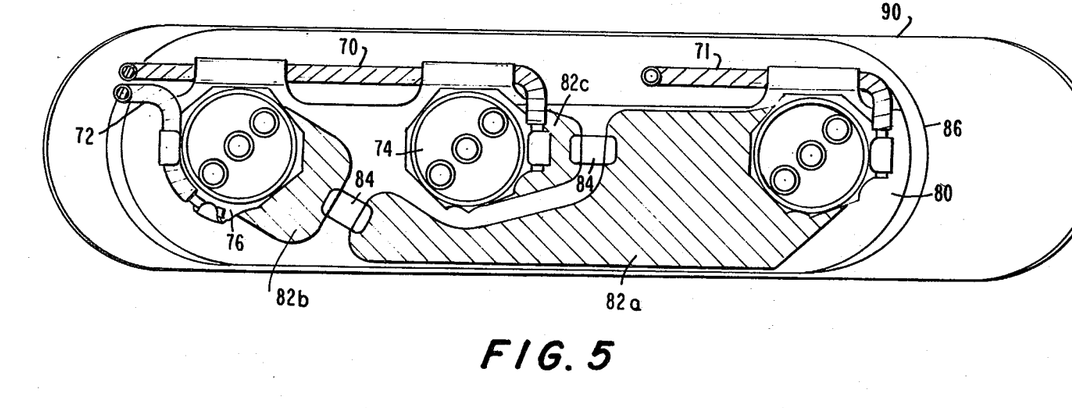
FIG. 5 is a bottom view of polyimide retainer 80 of FIG. 3 after it is folded over and with the wire connections having been made.

The numeral 80 represents a conventional polyimide flexible sheet which serves to retain wires 70 and 71, as is known in the art. The primary purpose of the sheet is well known in the art, and it will first be described without reference to the three metallization patterns 82a, 82b and 82c which are new. The forward half of the sheet is folded over as depicted by the arrow 81. Wires 70 and 71 are contained within the folds, as seen most clearly in FIG. 5 which is a view from the bottom after the sheet has been folded and after the mechanical connections have been made. It is seen that wires 70 and 71 are retained within the folds in the vicinity of holes 80g and 80h. The purpose of retaining the wires in this way is to prevent them from interfering with the sliding of the final assembly into case 40. As shown most clearly in FIG. 5, ground wire 71 is secured to one of the tab washers 76, which in turn is held in place when the respective one of nut terminals 74 is screwed onto the end of the pin which extends down from ground stud 96. Similar washers and nut terminals are provided for wires 70 and 72. It should be noted that after the retaining sheet 80 is folded over, holes 80a and 80f mate with each other, as do holes 80b and 80e, and holes 80c and 80d. These holes are necessary, of course, in order to allow the pins from the case cover to extend down to the nut terminals. It should also be noted that wire 72 is not retained by sheet 80 because in the illustrative embodiment of the invention the position of this wire was such that it could not interfere with insertion of the finished assembly into case 40.

In a conventional dual-chamber heart pacer, each stimulating electrode lead is coupled through a 150-pf RF filter capacitor to ground, as is known in the art. In accordance with one feature of my invention, these two filter capacitors are mounted directly on sheet 80 without the need to provide room for them on the printed circuit boards. The three metallization patterns which are fixed to sheet 80 are shown most clearly in FIG. 5. It is apparent that pattern 82a is connected to the grounded tab washer 76, pattern 82b is electrically connected to the pin which extends up to the atrial stimulating electrode terminal 92, and pattern 82c is electrically connected to the pin which extends up to ventricular stimulating electrode terminal 94. I provide two "chip" capacitors 84 which serve as the RF filter capacitors. Each of the capacitors has its end caps soldered directly to the grounded metallization pattern 82a and to one of the two other metallization patterns 82b or 82c. The net result is that the retaining sheet, which is needed anyway, can be made to serve in the additional capacity of supporting two RF filter capacitors, thereby eliminating the need for these capacitors to be mounted separately. The capacitors are quite small and do not extend down past nut terminals 74. Consequently, there is sufficient room for the two capacitors to be accommodated above the circuit board assembly.

FIG. 4 depicts some additional elements of the overall construction. The circuit board assembly 62 is wrapped with a sheet 64 to insulate the assembly from the case. The sheet is initially secured in place with a short section of adhesive polyimide tape 68. Sheet 64 is provided with a tab 64a on each side which extends down along a side of battery 46. These tabs serve to limit movement of the battery relative to the circuit board assembly so as to reduce the stress which might otherwise develop on the battery pins 48 and 50. Another polyimide adhesive tape 66 is then wrapped around and secured to sheet 64 and the battery 46.

Figure 8:
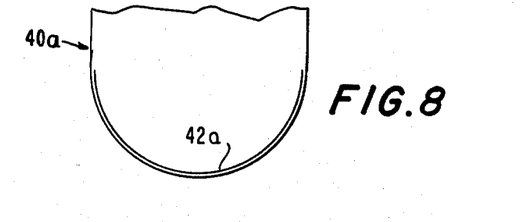
FIG. 8 depicts an alternative construction for a case having a rounded base.

The embodiment of FIG. 8 illustrates a case whose bottom end, along its wide dimension, is completely rounded. In such as case, sheet 42a should have a length equal to the length of a half circle whose radius is equal to the radius of the rounded base.

In general, the length of the constraining sheet and its width should be as described above so that the strip is self-locating at the bottom of the case (see FIG. 6); the sheet is automatically constrained to remain uniformly placed around the vertical axis of the unit, thus insuring that the spring force of the sheet is directed principally in the vertical direction so as to maximize the constraining force which holds all of the sub-assemblies in place. The force of the spring increases with its width and thickness, as well as the elastic modulus of the material of which the spring is made. The spring force can also be varied by pre-curving the strip. It is the curvature of the ends of the strip when the strip is placed in the case that tends to centrally align the strip in the case; it should be noted that while the case should thus have rounded edges, this is the universal practice because conventional battery casings for heart pacers have rounded edges. While it is not essential that the battery be located at the bottom of the unit, this is the preferred construction. However, it is to be understood that an appropriately shaped electronic assembly could be placed below the battery, the sheet 42 applying an upward force directly to the electronic assembly. It is also not necessary that the bottom of the case have rounded edges which have the same radii. Nor is it necessary that the case walls be parallel or flat. In some cases, it may be desirable to provide a little adhesive to locate the sheet 42. It is also possible to place the sheet at the bottom of shell 44 so that the force is exerted directly on the battery, rather than on the battery through the shell. It is also conceivable that in those cases where the electronic assembly and the battery are placed side-by-side, the use of a flat sheet, curved along its width, on the side of the unit could provide the necessary compression force.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A heart pacer comprising a case having an inner surface and an outer surface; a case cover sealed to the top of said case and containing at least one stimulating electrode terminal extending therethrough to the interior of said case; a power cell at the bottom of said case; and an electronic assembly positioned between, and connected to, said power cell and said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; at least one discrete component having its two ends connected to the two outer boards and passing through a hole in the middle board.

2. A heart pacer in accordance with claim 1 further characterized by no discrete component or integrated circuit package being contained on two adjacent boards.

3. A heart pacer in accordance with claim 1 having two stimulating electrode terminals and further comprising an insulating folded sheet of material positioned between said electronic assembly and said case cover and serving to retain to least one of two wires which connect said electronic assembly to said two stimulating electrode terminals; and further characterized by a first metallization pattern on said sheet which is electrically connected to the ground of the electronic assembly, second and third metallization patterns on said sheet which are electrically connected to said electronic assembly and to respective ones of said two stimulating electrode terminals, and a pair of RF filter capacitors each having its two ends soldered directly on said sheet, one end being soldered to said first metallization pattern and the other end being soldered to a respective one of said second and third metallization patterns.

4. A heart pacer comprising a case having an inner surface and an outer surface; a case cover sealed to the top of said case and containing at least one stimulating electrode terminal extending therethrough to the interior of said case; a power cell at the bottom of said case; the inner surface of the bottom of said case being curved and having a shape comparable to that of the outer surface of the bottom of said power cell; an electronic assembly positioned between, and connected to, said power cell and said at least one stimulating electrode terminal; and an insulating folded sheet of material positioned between said electronic assembly and said case cover and serving to retain at least one wire which connects said electronic assembly to said at least one stimulating electrode terminal; characterized by a first metallization pattern on said sheet which is electrically connected to the ground of the electronic assembly; a second metallization pattern on said sheet which is electrically connected to said electronic assembly and to said at least one stimulating electrode terminal; an RF filter capacitor having its two ends soldered directly on said sheet, each end being soldered to a respective one of said first and second metallization patterns; and a thin strip of resilient material positioned between the inner surface of the bottom of said case and the outer surface of the bottom of said power cell, said thin strip of material curving around at least one axis when said power cell is at the bottom of the sealed case and serving to apply opposing forces to said power cell and said case such that all elements within the sealed case are constrained against movement.

5. A heart pacer in accordance with claim 4 wherein the bottoms of said power cell and said case are curved such that said thin strip of material curves around an axis which is parallel with its length when said power cell is at the bottom of the sealed case.

6. A heart pacer comprising a case; a case cover sealed to the top of said case and containing at least one stimulating electrode terminal extending therethrough to the interior of said case; a power cell at the bottom of said case; an electronic assembly positioned between, and connected to, said power cell and said at least one stimulating electrode terminal; and an insulating folded sheet of material positioned between said electronic assembly and said case cover and serving to retain at least one wire which connects said electronic assembly to said at least one stimulating electrode terminal; characterized by a first metallization pattern on said sheet which is electrically connected to the ground of the electronic assembly, a second metallization pattern on said sheet which is electrically connected to said electronic assembly and to said at least one stimulating electrode terminal, and an RF filter capacitor having its two ends soldered directly on said sheet, each end being soldered to a respective one of said first and second metallization patterns.

7. A heart pacer comprising a case having an inner surface and an outer surface; a case cover sealed to the top of said case and containing at least one stimulating electrode terminal extending therethrough to the interior of said case; a power cell at the bottom of said said case; the inner surface of the bottom of said case being curved and having a shape comparable to that of the outer surface of the bottom of said power cell; and an electronic assembly positioned between, and connected to, said power cell and said at least one stimulating electrode terminal; characterized by a thin strip of resilient material positioned between the inner surface of the bottom of said case and the outer surface of the bottom of said power cell, said thin strip of material curving around at least one axis when said power cell is at the bottom of the sealed case and serving to apply opposing forces to said power cell and said case such that all elements within the sealed case are constrained against movement.

8. A heart pacer in accordance with claim 7 wherein the bottoms of said power cell and said case are curved such that said thin strip of material curves around an axis parallel with its length when said power cell is at the bottom of the sealed case.

9. A heart pacer comprising a case; a case cover sealed to the top of said case and containing at least one stimulating electrode terminal extending therethrough to the interior of said case; a power cell within said case; and an electronic assembly connected to said power cell and to said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; at least one discrete component having its two ends connected to the two outer boards and passing through a hole in the middle board.

10. A heart pacer in accordance with claim 9 further characterized by no discrete component or integrated circuit package being contained on two adjacent boards.

11. A heart pacer comprising a case; a case cover sealed to the top of said case and containing at least one stimulating electrode terminal extending therethrough to the interior of said case; a power cell within said case; an electronic assembly connected to said power cell and to said at least one stimulating electrode terminal; two mating surfaces within said case being curved and having complementary shapes; and an insulating folded sheet of material positioned between said electronic assembly and said case cover and serving to retain at least one wire which connects said electronic assembly to said at least one stimulating electrode terminal; characterized by a first metallization pattern on said sheet which is electrically connected to the ground of the electronic assembly; a second metallization pattern on said sheet which is electrically connected to said electronic assembly and to said at least one stimulating electrode terminal; and RF filter capacitor having its two ends soldered directly on said sheet, each end being soldered to a respective one of said first and second metallization patterns; and a thin strip of resilient material positioned between said two mating surfaces, said thin strip of material curving around at least one axis between said mating surfaces and serving to apply opposing forces to said two mating surfaces such that all elements within the sealed case are constrained against movement.

12. A heart pacer in accordance with claim 11 wherein said two mating surfaces are curved such that said thin strip of material curves around an axis which is parallel with the length of said strip of material between said two mating surfaces.

13. A heart pacer comprising a case; a case cover sealed to the top of said case and containing at least one stimulating electrode terminal extending therethrough to the interior of said case; a power cell within said case; an electronic assembly connected to said power cell and to said at least one stimulating electrode terminal; and an insulating folded sheet of material positioned between said electronic assembly and said case cover and serving to retain at least one wire which connects said electronic assembly to said at least one stimulating electrode terminal; characterized by a first metallization pattern on said sheet which is electrically connected to the ground of the electronic assembly, a second metallization pattern on said sheet which is electrically connected to said electronic assembly and to said at least one stimulating electrode terminal, and an RF filter capacitor having its two ends soldered directly on said sheet, each end being soldered to a respective one of said first and second metallization patterns.

14. A heart pacer comprising a case; a case cover sealed to the top of said case and containing at least one stimulating electrode terminal extending therethrough to the interior of said case; a power cell within said case; and an electronic assembly connected to said power cell and to said at least one stimulating electrode terminal; two mating surfaces within said case being curved and having complementary shapes; said two mating surfaces being curved around two axes; characterized by a thin strip of resilient material curving around two axes between said mating surfaces such that all elements within the sealed case are constrained against movement.

15. A heart pacer comprising a case having an inner surface and an outer surface; a case cover sealed to the top of said case and containing at least one stimulating electrode terminal extending therethrough to the interior of said case; a power cell at the bottom of said case; and an electronic assembly positioned between, and connected to, said power cell and said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; an insulating folded sheet of material positioned between said electronic assembly and said case cover and serving to retain at least one wire which connects said electronic assembly to said at least one stimulating electrode terminal; and a first metallization pattern on said sheet which is electrically connected to the ground of the electronic assembly, a second metallization pattern on said sheet which is electrically connected to said electronic assembly and to said at least one stimulating electrode terminal, and an RF filter capacitor having its two ends soldered directly on said sheet, each end being soldered to a respective one of said first and second metallization patterns.

16. A heart pacer in accordance with claim 15 wherein the inner surface of the bottom of said case is curved and has a shape comparable to that of the outer surface of the bottom of said power cell; and further characterized by a thin strip of resilient material positioned between the inner surface of the bottom of said case and the outer surface of the bottom of said power cell, said thin strip of material curving around at least one axis when said power cell is at the bottom of the sealed case and serving to apply opposing forces to said power cell and said case such that all elements within the sealed case are constrained against movement.

17. A heart pacer in accordance with claim 16 wherein the bottoms of said power cell and said case are curved around an axis which is parallel with the length of said strip of material.

18. A heart pacer comprising a case having an inner surface and an outer surface; a case cover sealed to the top of said case and containing at least two stimulating electrode terminals extending therethrough to the interior of said case; a power cell at the bottom of said case; and an electronic assembly positioned between, and connected to, said power cell and said at least two stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; an insulating folded sheet of material positioned between said electronic assembly and said case cover and serving to retain at least one of two wires which connect said electronic assembly to said two stimulating electrode terminals; and a first metallization pattern on said sheet which is electrically connected to the ground of the electronic assembly, second and third metallization patterns on said sheet which are electrically connected to said electronic assembly and to respective ones of said two stimulating electrode terminals, and a pair of RF filter capacitors each having its two ends soldered directly on said sheet, one end being soldered to said first metallization pattern and the other end being soldered to a respective one of said second and third metallization patterns.

19. A heart pacer comprising a case having an inner surface and an outer surface; a case cover sealed to the top of said case and containing at least one stimulating electrode terminal extending therethrough to the interior of said case; a power cell at the bottom of said case; and an electronic assembly positioned between; and connected to, said power cell and said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; an insulating folded sheet of material positioned between said electronic assembly and said case cover and serving to retain at least one wire which connects said electronic assembly to said at least one stimulating electrode terminal; and a first metallization pattern on said sheet which is electrically connected to the ground of the electronic assembly, a second metallization pattern on said sheet which is electrically connected to said electronic assembly and to said at least one stimulating electrode terminal, and an RF filter capacitor having its two ends soldered directly on said sheet, each end being soldered to a respective one of said first and second metallizaton patterns.

20. A heart pacer in accordance with claim 19 wherein the inner surface of the bottom of said case is curved and has a shape comparable to that of the outer surface of the bottom of said power cell; and further characterized by a thin strip of resilient material positioned between the inner surface of the bottom of said case and the outer surface of the bottom of said power cell, said thin strip of material curving around at least one axis when said power cell is at the bottom of the sealed case and serving to apply opposing forces to said power cell and said case such that all elements within the sealed case are contrained against movement.

21. A heart pacer in accordance with claim 20 wherein the bottoms of said power cell and said case are curved such that said thin strip of material curves around an axis which is parallel with its length when said power cell is at the bottom of the sealed case.

22. A heart pacer comprising a case having an inner surface and an outer surface; a case cover sealed to the top of said case and containing at least one stimulating electrode terminal extending therethrough to the interior of said case; a power cell at the bottom of said case; and an electronic assembly positioned between, and connected to, said power cell and said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being grated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; the inner surface of the bottom of said case being curved and having a shape comparable to that of the outer surface of the bottom of said power cell; and a thin strip of resilient material positioned between the inner surface of the bottom of said case and the outer surface of the bottom of said power cell, said thin strip of material curving around at least one axis when power cell is at the bottom of the sealed case and serving to apply opposing forces to said power cell and said case such that all elements within the sealed case are constrained against movement.

23. A heart pacer in accordance with claim 22 wherein the bottoms of said power cell and said case are curved such that said thin strip of material curves around an axis which is parallel with its length when said power cell is at the bottom of the sealed case.

24. A heart pacer comprising a case; a case cover sealed to the top of said case and containing at least one stimulating electrode terminal extending therethrough to the interior of said case; a power cell within said case; and an electronic assembly connected to said power cell and to said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; an insulating folded sheet of material positioned between said electronic assembly and said case cover and serving to retain at least one wire which connects said electronic assembly to said at least one stimulating electrode terminal; and a first metallization pattern on said sheet which is electrically connected to the ground of the electronic assembly, a second metallization pattern on said sheet which is electrically connected to said electronic assembly and to said at least one stimulating electrode terminal, and an RF filter capacitor having its two ends soldered directly on said sheet, each end being soldered to a respective one of said first and second metallization patterns.

25. A heart pacer in accordance with claim 24 wherein two mating surfaces within said case are curved and have complementary shapes; and further characterized by a thin strip of resilient material positioned between said two mating surfaces, said thin strip of material curving around at least one axis between said mating surfaces and serving to apply opposing forces to said two mating surfaces such that all elements within the sealed case are constrained against movement.

26. A heart pacer in accordance with claim 25 wherein said two mating surfaces are curved such that said thin strip of material curves around an axis which is parallel with the length of said strip of material between said two mating surfaces.

27. A heart pacer comprising a case; a case cover sealed to the top of said case and containing at least one stimulating electrode terminal extending therethrough to the interior of said case; a power cell within said case; and an electronic assembly connected to said power cell and to said at least one stimulating electrode terminal; characterized by said electronic assembly having three printed circuit boards arranged in parallel with each other and mechanically fixed relative to each other by cross-wires which electrically connect the circuit boards to each other; each of a vast majority of discrete components and integrated circuit packages in said electronic assembly being contained completely on only one of said boards; two sets of discrete components and integrated circuit packages being contained on two respective adjacent boards, with the two sets facing each other and one set being arranged on its respective board to extend into spaces between the discrete components and integrated circuit packages of the set on the other board such that the two boards are separated by a distance which is approximately equal to the height of the highest discrete component or integrated circuit package of all those contained on the two boards; two mating surfaces within said case being curved and having complementary shapes; and a thin strip of resilient material positioned between said two mating surfaces, said thin strip of material curving around at least one axis between said mating surfaces and serving to apply opposing forces to said two mating surfaces such that all elements within the sealed case are constrained against movement.

* * * * *